(12) United States Patent
Nordin et al.

(10) Patent No.: US 8,243,943 B2
(45) Date of Patent: Aug. 14, 2012

(54) HEARING PROTECTOR WITH REMOVABLE MICROPHONE, AMPLIFIER, AND LOUDSPEAKER UNIT

(75) Inventors: Henrik Nordin, Forsheda (SE); Sigvard Nilsson, Värnamo (SE)

(73) Assignee: 3M Svenska Aktiebolag (SE)

( * ) Notice: Subject to any disclaimer, the term of this patent is extended or adjusted under 35 U.S.C. 154(b) by 180 days.

(21) Appl. No.: 10/580,923

(22) PCT Filed: Nov. 23, 2004

(86) PCT No.: PCT/SE2004/001709
§ 371 (c)(1),
(2), (4) Date: Feb. 12, 2007

(87) PCT Pub. No.: WO2005/051255
PCT Pub. Date: Jun. 9, 2005

(65) Prior Publication Data
US 2007/0274529 A1    Nov. 29, 2007

(30) Foreign Application Priority Data
Nov. 27, 2003    (SE) ........................................ 0303189

(51) Int. Cl.
*A61F 11/06*    (2006.01)
*H04R 25/00*    (2006.01)
(52) U.S. Cl. ............................. 381/72; 381/371; 381/375
(58) Field of Classification Search .................... 381/72, 381/57, 71.6, 71.7, 371, 383, 384, 370, 374, 381/375, 376, 309
See application file for complete search history.

(56) References Cited

U.S. PATENT DOCUMENTS

| | | | |
|---|---|---|---|
| 2,235,372 A | 3/1941 | Kalbitz | |
| 3,087,028 A | 4/1963 | Bonnin | |
| 3,306,991 A * | 2/1967 | Wood | 381/72 |
| 3,394,226 A * | 7/1968 | Andrews, Jr. | 381/72 |
| 3,456,263 A | 7/1969 | Aileo | |
| 3,579,640 A | 2/1970 | Beguin | |
| 3,833,939 A | 9/1974 | Dostourian | |
| 3,869,584 A | 3/1975 | Wilde | |

(Continued)

FOREIGN PATENT DOCUMENTS

DE    10117704    6/2001

(Continued)

OTHER PUBLICATIONS

International Search Report; PCT/SE2004/001709; Mar. 4, 2005 (all references in search report listed above).

*Primary Examiner* — Yuwen Pan
*Assistant Examiner* — Kile Blair
(74) *Attorney, Agent, or Firm* — Emily M. Van Vliet

(57) ABSTRACT

A hearing protector comprises a hearing hood (2), a microphone (7), a loudspeaker and an amplifier. The hearing hood (2) has passive noise damping. The microphone (7) is disposed exteriorly on the hearing protector, while the loudspeaker is disposed inside the hood. The amplifier amplifies and transmits the signals from the microphone (7) to the loudspeaker. The noise damping of the hearing hood (2) is broad band. The frequency range of the amplifier corresponds to the frequency range of human speech. The amplification of the amplifier is variable and the greatest amplification is such that the sum total of the sound levels that are caused, on the one hand, by ambient sound passing through the hood (2) and, on the other hand, by sound from the loudspeaker amounts to a maximum, predetermined value.

5 Claims, 4 Drawing Sheets

U.S. PATENT DOCUMENTS

| | | | |
|---|---|---|---|
| 3,890,474 A * | 6/1975 | Glicksberg | 381/72 |
| 3,952,158 A * | 4/1976 | Kyle et al. | 381/72 |
| 4,027,113 A | 5/1977 | Matsumoto | |
| 4,064,362 A * | 12/1977 | Williams | 381/72 |
| 4,066,849 A | 1/1978 | Chladil, Sr. | |
| 4,087,653 A | 5/1978 | Frieder, Jr. | |
| 4,302,635 A | 11/1981 | Jacobsen | |
| 4,327,257 A | 4/1982 | Schwartz | |
| 4,677,678 A | 6/1987 | McCutchen | |
| 4,829,571 A | 5/1989 | Kakiuchi | |
| 4,833,719 A | 5/1989 | Carme | |
| 4,867,149 A | 9/1989 | Falco | |
| 4,928,311 A * | 5/1990 | Trompler | 381/72 |
| 4,965,836 A | 10/1990 | Andre | |
| 4,985,925 A | 1/1991 | Langberg | |
| 5,125,032 A * | 6/1992 | Meister et al. | 381/72 |
| 5,181,252 A | 1/1993 | Sapiejewski | |
| 5,251,263 A | 10/1993 | Andrea | |
| 5,402,497 A | 3/1995 | Nishimoto | |
| 5,497,427 A | 3/1996 | Nageno | |
| 5,519,783 A | 5/1996 | Kumar | |
| 5,550,923 A | 8/1996 | Hotvet | |
| 5,631,965 A * | 5/1997 | Chang et al. | 381/72 |
| 5,675,658 A * | 10/1997 | Brittain | 381/72 |
| 6,631,279 B2 | 10/2003 | Rivera | |
| 6,704,428 B1 | 3/2004 | Wurtz | |
| 6,724,906 B2 | 4/2004 | Naksen | |
| 6,728,388 B1 | 4/2004 | Nageno | |
| 6,748,087 B1 | 6/2004 | Jones | |
| 6,801,629 B2 | 10/2004 | Brimhall | |
| 6,965,681 B2 | 11/2005 | Almqvist | |
| 6,970,571 B2 | 11/2005 | Knorr | |
| 7,099,485 B2 | 8/2006 | Dittli | |
| 7,245,735 B2 | 7/2007 | Han | |
| 7,308,106 B2 | 12/2007 | Vaudrey | |
| 7,327,850 B2 | 2/2008 | Crump | |
| 7,391,878 B2 | 6/2008 | Liao | |
| 7,664,282 B2 | 2/2010 | Urso | |
| 8,130,971 B2 * | 3/2012 | Werner | 381/72 |
| 2001/0046304 A1 | 11/2001 | Rast | |
| 2002/0001391 A1 | 1/2002 | Darbut | |
| 2002/0003889 A1 | 1/2002 | Fischer | |
| 2002/0080979 A1 * | 6/2002 | Brimhall et al. | 381/72 |
| 2002/0080987 A1 * | 6/2002 | Almqvist | 381/371 |
| 2003/0223612 A1 * | 12/2003 | Knorr et al. | 381/370 |
| 2004/0125976 A1 | 7/2004 | Reneker | |
| 2004/0125977 A1 | 7/2004 | Hong | |
| 2004/0258253 A1 * | 12/2004 | Wurtz | 381/71.6 |
| 2005/0013447 A1 * | 1/2005 | Crump et al. | 381/71.6 |
| 2007/0183606 A1 * | 8/2007 | Doty | 381/72 |
| 2007/0274529 A1 | 11/2007 | Nordin et al. | |
| 2008/0011084 A1 | 1/2008 | Von Dach | |
| 2008/0192973 A1 | 8/2008 | Heringslack | |
| 2008/0279411 A1 | 11/2008 | Suzuki | |
| 2011/0124300 A1 | 5/2011 | Sinai | |

FOREIGN PATENT DOCUMENTS

| | | |
|---|---|---|
| EP | 0465971 A2 | 1/1992 |
| EP | 0967592 | 12/1999 |
| EP | 1629808 A1 | 3/2006 |
| FR | 2695302 | 3/1994 |
| GB | 1160431 | 8/1969 |
| GB | 1289993 A | 9/1972 |
| GB | 2445984 A | 7/2008 |
| WO | WO 8704065 | 7/1987 |
| WO | WO 9107153 | 5/1991 |
| WO | WO 96/08004 | 3/1996 |
| WO | WO 97/28742 A1 | 8/1997 |
| WO | WO 02/17838 | 3/2002 |
| WO | WO 03/086124 | 10/2003 |
| WO | WO 2005/051255 | 6/2005 |
| WO | WO 2006/118514 | 11/2006 |
| WO | WO 2008/099137 | 8/2008 |
| WO | WO 2008/113822 | 9/2008 |

* cited by examiner

HEARING PROTECTOR WITH REMOVABLE MICROPHONE, AMPLIFIER, AND LOUDSPEAKER UNIT

TECHNICAL FIELD

The present invention relates to a hearing protector comprising a hearing hood with passive noise damping, a microphone disposed exteriorly on the hearing protector, a loudspeaker disposed inside the hood and an amplifier for amplifying sound signals caused by the microphone and transmitting the signals to the loudspeaker.

BACKGROUND ART

Hearing protectors are often employed in noisy environments, such as factories, airports etc. Such hearing protectors consist of two muffs or hoods manufactured from hard material, for example plastic, which sealingly surround the ears of the wearer and which are connected to one another by the intermediary of a headband. Interiorly in the muffs or hoods, there is provided as a rule a porous noise absorbent agent. The employment of hearing protectors has increased at the same rate as awareness has grown of the risks of loss of hearing caused by noise, and developments are constantly being made of the hearing protectors which occur on the market in order to make them more user-friendly, so that the desired level of use is encouraged. The majority of hearing protectors utilise so-called passive damping, i.e. a damping that takes place with the aid of the material included in the muffs or hoods and noise absorbent agents disposed in them.

A remaining problem in the employment of hearing protectors is that there is often a need to listen to requisite sound, such as instructions, or other conversations from a person in the vicinity, at the same time as the intention is to impede as much background noise as possible.

Hearing protectors occur on the market which, in response to the level, damp noise above a certain sound level. In this level-dependent damping, the hearing protector allows the passage of all sound up to a pre-determined sound level, with the aid of a microphone, an amplifier and a loudspeaker disposed inside the hearing muff or hood. When this level is exceeded, the electronics are shut off and all sound is damped by passive damping.

There also occur different types of communication systems in connection with hearing protection. For example, all people in factory premises may be provided with hearing protection which includes a radio receiver. The radio transmissions that can be received are often standard radio channels, but may also include or consist of a local transmission at the company in question. By such means, centrally transmitted instructions, alerts and other information are received as a one-way communication, but the system does not satisfy the need for communication between the individual recipients.

A problem common to existing hearing protectors is that they are not used in those cases where they are experienced as being inconvenient to use. Instead, there is a tendency that the user quite simply removes the hearing protector when s/he wishes to talk to someone else, for example to receive instructions or the like. Thereafter, there is a major risk that the wearer forgets to replace the hearing protector, with a consequential increase in the risk of loss of hearing through noise.

BRIEF SUMMARY OF THE INVENTION

The invention provides a hearing protector which affords the possibility of selective communication, in which event the hearing protector should be so simple to use that the risk of loss of hearing through noise is minimised. At the same time, the audible sensitivity to speech should be maximised when communication is desired.

The hearing protector of the invention provides that the noise damping of the hearing hood is broad-band, that the amplifier has variable amplification and frequency range which corresponds to the frequency range of human speech, and that the amplifier has a maximum predetermined amplification, where the sum total of the sound levels that are caused, on the one hand by ambient sound passing through the hood, and on the other hand by sound emitted by the loudspeaker amounts to a maximum predetermined value.

Further advantages will be attained if the hearing protector according to the present invention is further given one or more of the characterising features as set forth in the appended claims.

BRIEF DESCRIPTION OF THE ACCOMPANYING DRAWINGS

The present invention will now be described in greater detail hereinbelow, with reference to the accompanying Drawings. In the accompanying Drawings.

DETAILED DESCRIPTION OF THE INVENTION

Figure 1:
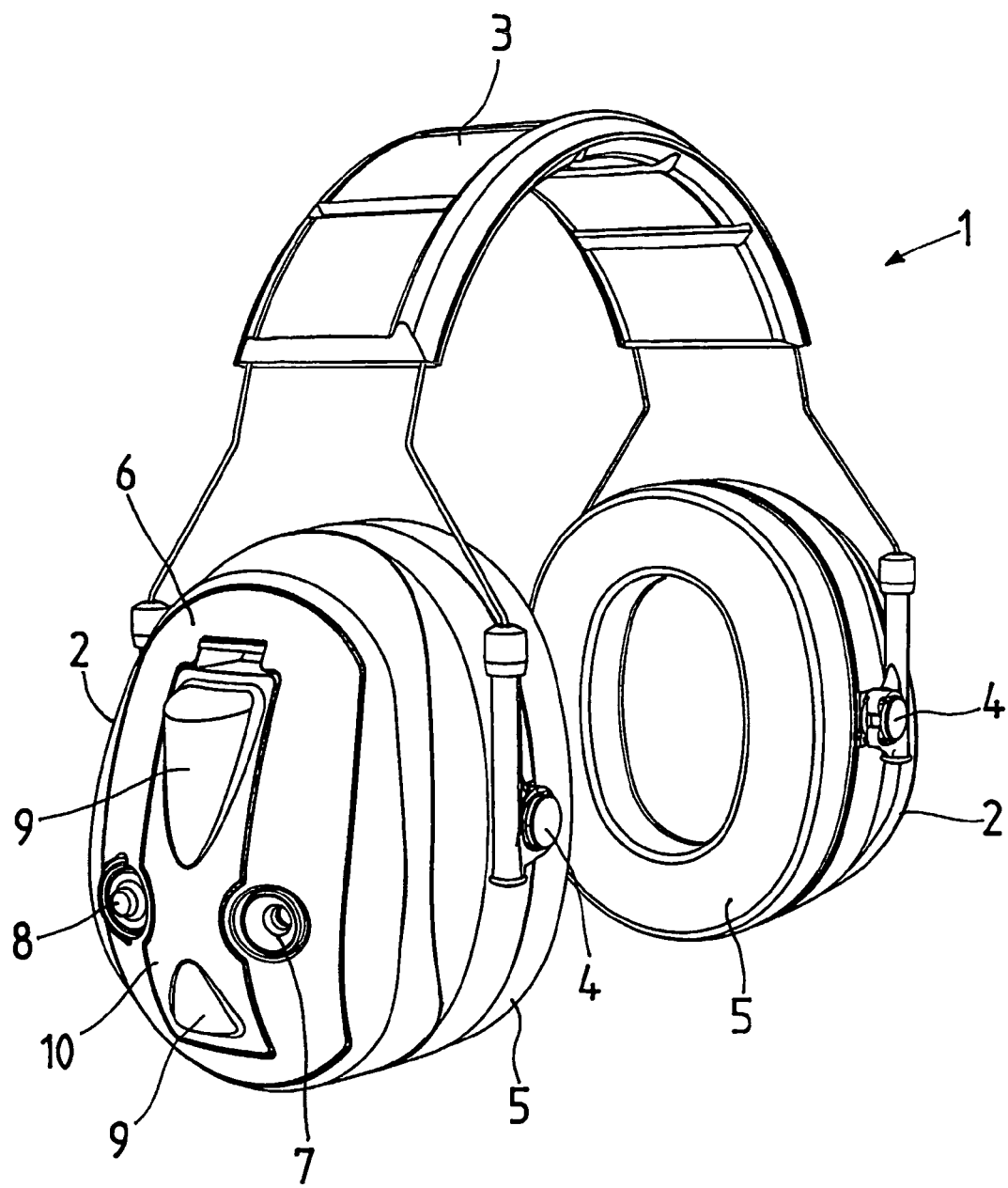
FIG. 1 is a perspective view of a hearing protector according to the present invention.

FIG. 1 shows a hearing protector 1 according to the present invention. The hearing protector 1 includes, in the usual manner, two hearing protector muffs or hoods 2 and a stirrup shaped headband 3 which unites the two hoods 2. On each side of each respective hood 2, there is provided a pivot 4 which connects the hoods 2 pivotally to the headband 3.

The hoods 2 have hard outer shells and a damping interior which may be provided in a manner that is previously known in the art. For example, the hoods 2 may be provided with double shells or some other type of passive noise damping. Further, the hoods 2 each display a sealing ring 5 for abutment against the head of the user around the user's ears. The sealing rings 5 may be designed in any optional manner which is previously known in the art.

According to the present invention, at least the one hood 2 has a unit 6 which makes for communication to the person wearing the hearing protector. The unit comprises a microphone 7 disposed exteriorly on the hood 2, an electronics unit with an amplifier with variable amplification and possibly adjustable band width, as well as a loudspeaker 28 (FIGS. 5 and 6) disposed interiorly in the hood. The unit, which may be removable, but also integrated in the hood 2, further includes a battery hatch 10 which covers a recess 12 and which has a bulge 9 for accommodating a battery (not shown).

The microphone 7 is preferably a microphone possessing no particular directional effect, in other words a so-called broadcast microphone 7. This implies that the microphone 7 per se has the capability to take up sound regardless of the position of the source of the sound in relation to the microphone 7. The positioning of the microphone 7 should also be such that its function is not essentially affected by the direction in which the hearing protector 1 is turned for maximum flexibility in the use thereof. In this case, the microphone, as is clearly apparent from FIG. 1, is laterally directed in relation to the head of the wearer of the hearing protector.

In certain cases, a forwardly directed positioning of the microphone 7 may be preferred. In this embodiment, the microphone is directionally active and is turned to face towards a person standing in front of and speaking to the wearer of the hearing protector.

An activator button 8 is provided and is designed so that it is readily accessible by the user. The positioning of this button should also be such that it functions equally well regardless of in which direction the hearing protector is facing. This implies that a satisfactory function of one and the same hearing protector will be attained regardless of whether the user is right-handed or left-handed or whether the user, for one reason or another, wears the hearing protector back-to-front.

Figure 2:
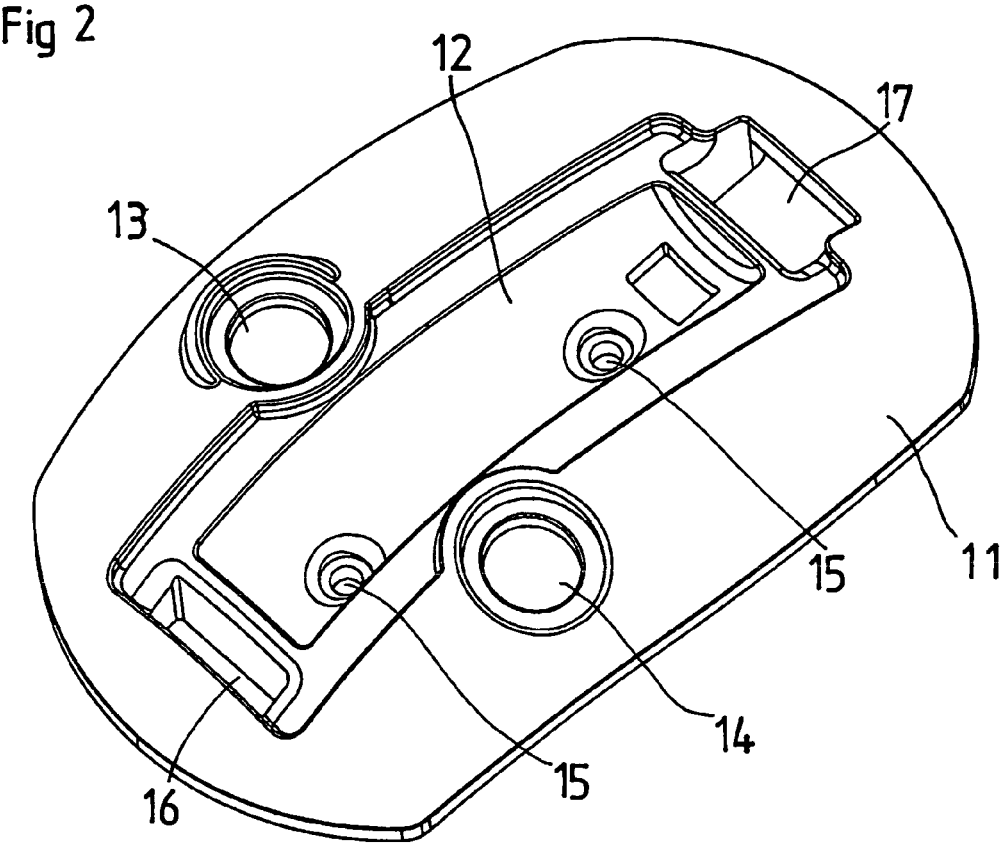
FIG. 2 is a perspective view of a lid for a removable unit included in the hearing protector, a battery hatch not being shown in the Figure.

FIG. 2 shows a covering plate for the removable unit 6. The covering plate or lid has a recess 12 in the form of a depression for accommodating a battery. In the bottom of the recess 12, there are provided, in the preferred embodiment, two holes 15 for screws or similar fixing devices such as, for example, flanging. Above and below the recess 12, there are provided two substantially rectangular depressions 16 and 17. These depressions are intended for fixing a hatch 10 which covers the battery and which displays the above-mentioned bulge 9.

Further, the covering plate 11 has a recess 13 for accommodating the operating device in the form of the activator button 8. A similar recess 14 is disposed on the opposing side of the battery recess 12 for accommodating the microphone 7 provided in the removable unit 6.

The removable unit 6 also includes a loudspeaker and electronic components for realising both amplification and broad-band restriction of incoming sonic signals and a timer function for shutting off the electronics after a given predetermined time.

Figure 3:
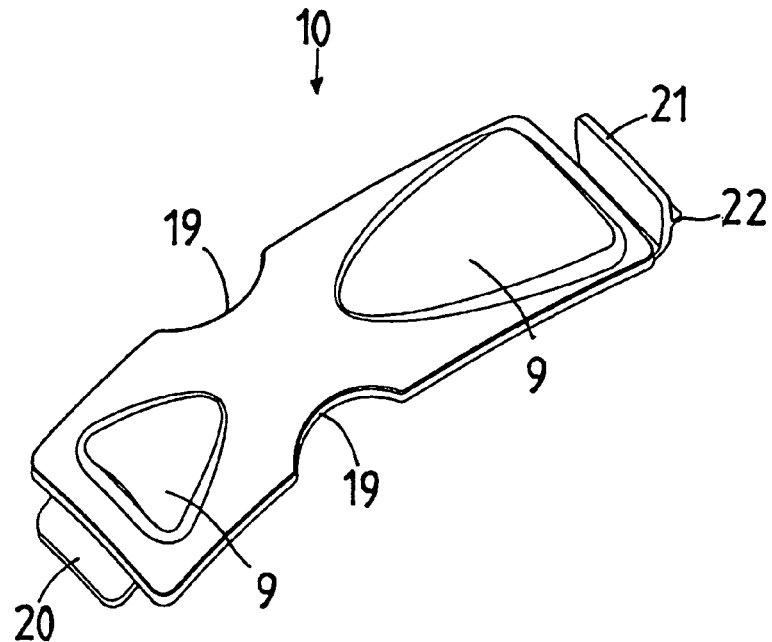
FIG. 3 is a perspective view of the battery hatch which is omitted from FIG. 2.

FIG. 3 shows the battery hatch 10 which is intended to cover the battery when this is housed in the recess 12. The battery hatch 10 has bulges 9 which correspond to the configuration of the battery in those regions which extend outside the major plane of the covering plate 11 and the battery hatch 11. The hatch further displays lower 20 and upper 21 fixing members for an openable fixing of the battery hatch 10. The lower fixing member 20 is a substantially planar projection which is intended to be received in a corresponding recess in the covering plate 11. the upper fixing member 21 displays a substantially U-shaped cross section, whose free shank may be actuated in a direction towards the battery hatch 10 for releasing the hatch 10 from the covering plate 11. On its side facing away from the battery hatch 10, the upper fixing member 21 has a longitudinal, catch-shaped member 22 which is disposed to pass the edge of the depression 17 when the upper fixing member is actuated inwardly in a direction towards the battery hatch 10. The catch-shaped member 22 thus snaps in behind the edge of the depression 17.

Figure 4:
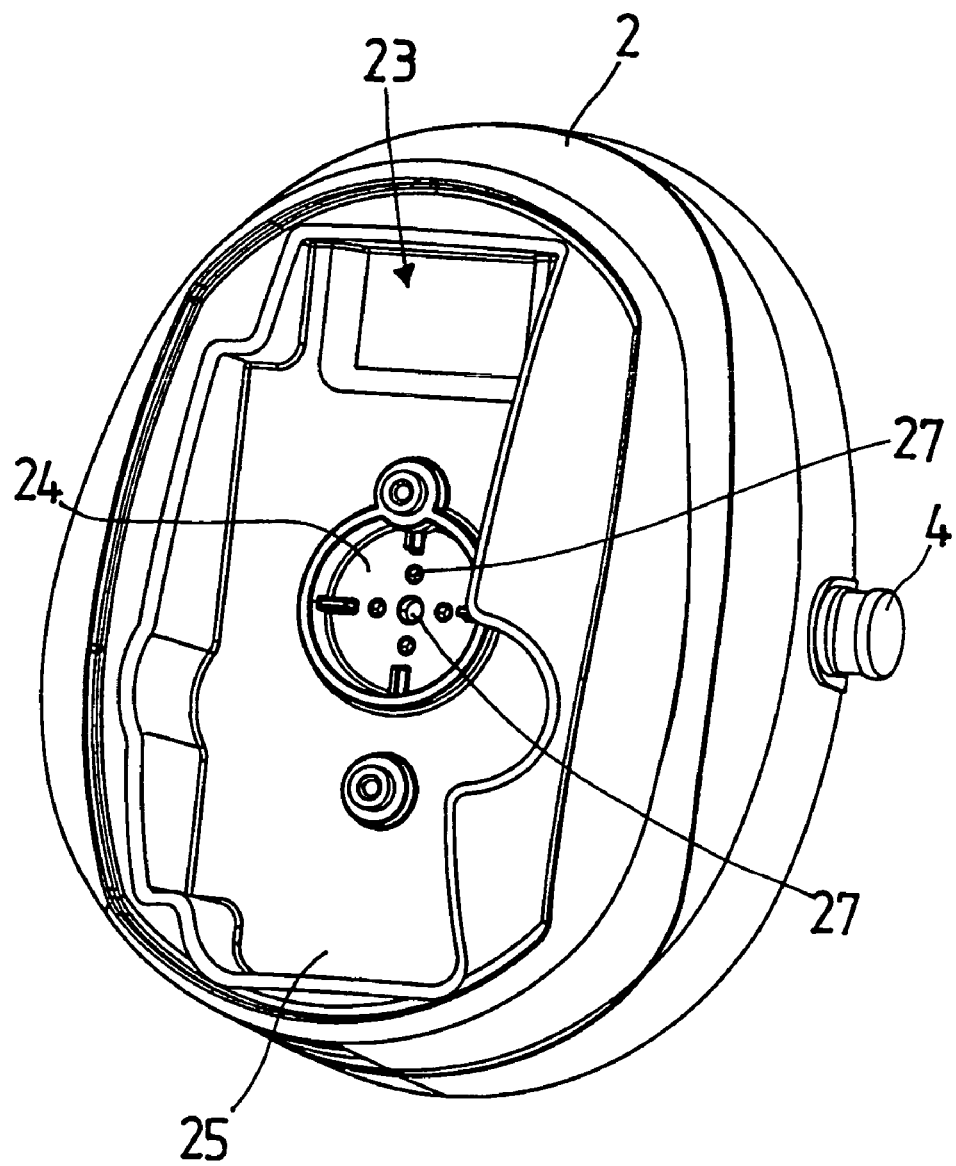
FIG. 4 is a perspective view of a hearing muff or hood included in the hearing protector, where the removable unit has been removed.

FIG. 4 shows one of the hearing hoods 2 seen from the outside and without the removable unit 6. Thus, the hearing hood 2 has a quite large recess 23 for receiving the removable unit 6. The recess 23 has a bottom wall 25 and is designed so as to afford room for the removable unit 6 with, for example, its recess 13 for the actuator member, the recess 14 for the microphone 7 as well as the depressions for the fixing members 20, 21 of the battery hatch 10. In the bottom 25 of the recess 23, there is further provided a perforated recess 24 for the loudspeaker facing towards the inside of the hearing hood 2. In principle, the bottom 25 functions as a partition between the recess 23 and the inside of the hearing hood 2.

The fact that the perforations 27 are placed in the bottom of the recess 23 implies that they are also placed close to the opening of the acoustic meatus of the wearer. This entails that the sound from the loudspeaker will be perceived as more dominant in relation to the ambient noise which penetrates through the hearing hood, for which reason the amplification by the amplifier may be made weaker without any deterioration of the audibility of the spoken word emitted by the loudspeaker. This implies less electric power consumption and consequentially a longer service life for the batteries.

The properties of the bottom 25 correspond to those of the outer defining wall of the hearing hood 2, i.e. the removable unit 6 is functionally disposed on the outside of the hearing hood 2, while, in terms of appearance, it is recessed in the hearing hood 2. Consequently, in order to keep the bottom tight against the outside and prevent noise coming from outside from being allowed through the perforation 27, the portion of the removable unit 6 around the loudspeaker sealingly abuts against the edge of the depression 24. The sealing abutment may be realised in any optional manner which is previously known in the art.

Since the bottom 25 is to be considered as a part of the defining wall of the hood 2, no further seals are required between the removable unit 6 and the edge of the recess 23. Nor is it necessary to provide any special sealing at the battery hatch 10.

The removable unit 6, which is not shown in FIG. 4, may be designed as a standard unit. This implies that the same removable unit 6 may be employed together with a large number of different hoods 2 possessing different passive damping properties, which reduces the need for storekeeping of parts and provides a possibility to adapt the hearing protector in response to different noisy environments.

The hearing protector 1 functions as follows:

On those occasions when the user wishes to listen to someone or something, the activator button 8 is depressed, which activates the microphone 7 and the associated amplifier which transmits sound to the inwardly directed loudspeaker. The sound taken up by the microphone 7, i.e. preferably speech, is amplified to a suitable sound level inside the hearing protector. Any possible background noise is amplified as little as possible. When the communication is completed and the reception of more sound signals from the microphone 7 is no long required, the electronics are deactivated by the release of the activator button 8. An alternative to manual deactivation is that the electronics in the hearing protector 1 automatically shut off the loudspeaker after a given time lapse.

The automatic shut off is realised in practice with the aid of a special delay circuit which, after a predetermined time lapse from activation once again shuts off the electronics of the hearing protector. In the preferred embodiment, the time delay is about 20 seconds. If the intention is to interrupt communication earlier, the electronics are manually shut off by once again depressing the activator button 8. A variation where the activator button 8 is held depressed continuously for a longer period of time and the automatic shut off is disabled while the button is held depressed is less satisfactory since the deactivation function would then be rendered inoperative, for example in that the button 8 is taped down.

The electronics in the unit are formed in such a manner that they display a variable amplification of the incoming signal via the microphone 7, where the level of amplification is varied so that the higher the sound level that is sensed by the electronics, the lower will be the level of amplification. The amplification is limited to a value where the level of the sound emitted by the loudspeaker together with the level of the ambient noise that penetrates through the protector hood amounts to such a maximum predetermined value as is considered tolerable in view of the risk of loss of hearing due to noise. If the penetrating ambient noise alone reaches this value, the electronics are kept disabled so that the loudspeaker is silent.

The hearing protector hood per se displays passive noise damping with large band width. As a result, ambient noise is damped within a broad frequency range. Customised adaptation to certain noisy environments, with particularly good damping in certain frequency bands can naturally be put into effect. One example might be noisy environments with very low frequencies.

The protector hood 2 also displays frequency limitation for those frequencies that are amplified via the electronics. The interesting range for understanding the spoken word extends from 125 to 6000 Hz. The focal point lies between these extreme limits, for which reason the preferred system of microphone 7, loudspeaker 28 and amplifier preferably operates in the range of from about 500 Hz to 3500 Hz, i.e. within the frequency range of human speech. These limits are merely exemplified, for which reason the figure values may vary, depending on the steepness of the filters which are employed for the frequency limitation.

According to the present invention, it is possible to vary, within the pass band of the electronics, the amplification according to frequency so that a "equaliser effect" is achieved and as a result the understanding of spoken sound transmitted via the electronics will be optimised.

The hearing protector 1 possesses, as was mentioned above, passive damping. The passive damping is frequency-responsive and is affected by the appearance, design and other properties of the hood 2. In order for the present invention to be usable, the protector hood 2 should be of such a type that in itself damps noise effectively.

In the preferred embodiment, a given configuration of the unit 6 was shown. It is naturally possible to vary the appearance of this unit in innumerable different ways, as well as to design it as an integral part of the hood proper.

Figure 5:
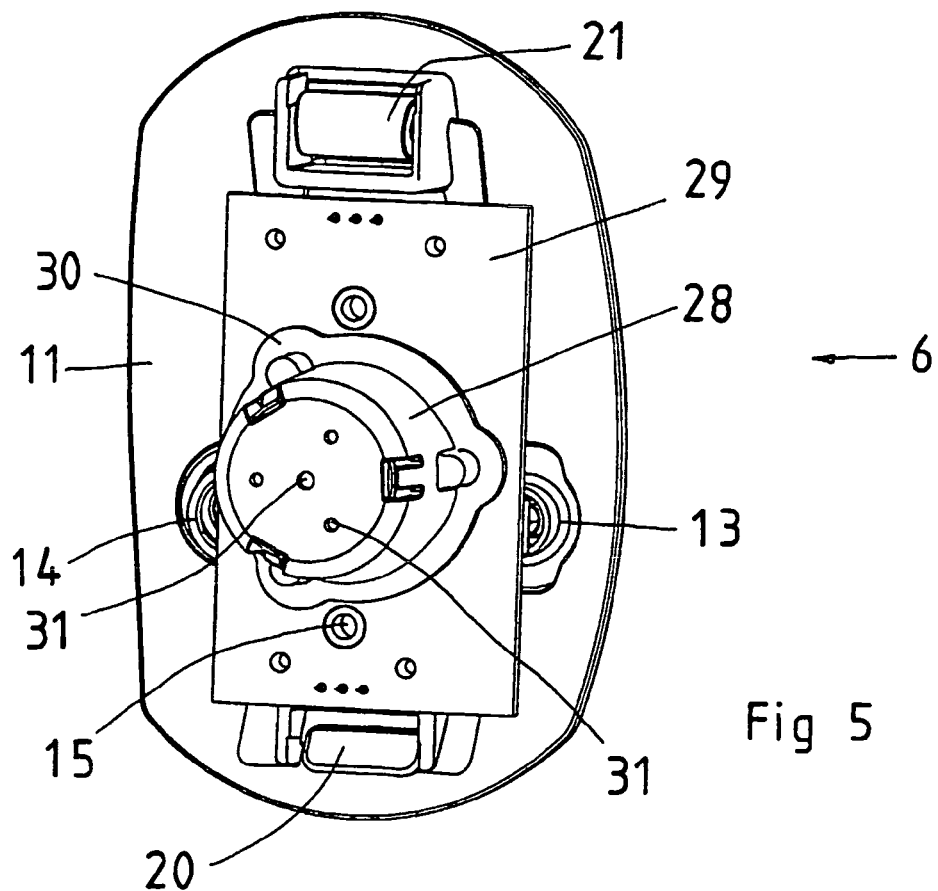
FIG. 5 is a perspective view of a unit intended for mounting in a hearing hood, in a second embodiment of the present invention.
Figure 6:
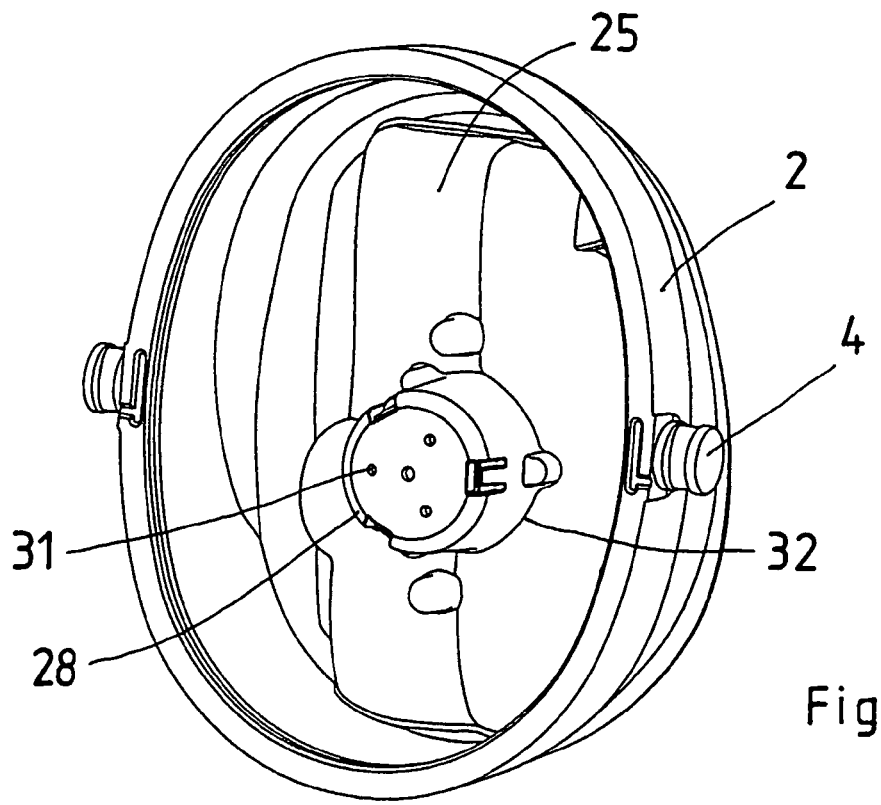
FIG. 6 is a perspective view of the hearing protector shown from the inside, with the unit of FIG. 5 mounted in position.

FIGS. 5 and 6 show an alternative embodiment of the unit which per se includes means for frequency-responsive amplification of the signal taken up by the microphone 7 disposed on the outside of the protector hood 2. It will be apparent from the Figure that the unit includes a covering plate 11 which, on its rear side (inside), carries a circuit card 29 with the electronics circuits necessary according to the present invention. It will further be apparent that the loudspeaker 28 is secured on that side of the circuit card 29 which is turned to face in towards the interior of the protector hood 2. Around the loudspeaker 28, there is disposed a sealing or gasket ring 30 which is intended to seal against the outside of a partition in the hood, where this partition corresponds to the bottom wall 25 in the recess 23 illustrated in FIG. 4. The loudspeaker has a number of apertures 31 through which the sound produced by the loudspeaker may pass to the interior of the protector hood 2. On the rear side of the membrane of the loudspeaker, there is a minor volume which to some degree damps the base range of the sound emitted by the loudspeaker.

It will be apparent from FIG. 6 that the wall 25 which forms the bottom of the recess 23 which is intended for accommodating the unit 6 from the outside of the hood is closed towards the inside of the hood 2. It will be particularly apparent that the opening 32 through which the loudspeaker 28 extends displays a close fit with the periphery of the loudspeaker. Since the sealing ring 30 on the circuit card 29 connects around the loudspeaker 28 to the outside of the wall 25, it will be readily perceived that the sealing-off of the interior of the hood to the ambient surroundings will be thorough.

It will further be apparent from FIG. 6 that the loudspeaker 28 extends in a considerable distance into the interior of the hood 2 so that its sound apertures 31 will be located proximal the opening of the acoustic meatus of the wearer of the hearing protector. In one embodiment, where the microphone 7 is turned to face forwards, it is suitably designed with superior directional effect so that the pick-up lobe of the microphone may be directed towards the face of a person standing in front of and speaking to the wearer of the hearing protector. As a result, it is possible to restrict the take-up of ambient noise via the microphone 7 and thereby increase the level of understanding in the communication between the two people.

What is claimed is:

1. A hearing protector comprising
a hearing hood with passive noise damping,
a microphone disposed exteriorly on the hearing protector,
a loudspeaker, and
an amplifier for amplifying sound signals caught by the microphone and passing the signals on to the loudspeaker,
wherein the microphone, amplifier, and loudspeaker are disposed together as a standard removable unit which is insertable in a recess disposed in an outside surface of the hearing hood, with a bottom wall being a closed partition between the recess and an interior of the hearing hood, the bottom wall having a depression inclusive of at least one opening and configured for disposal of the loudspeaker therein, said depression facing towards an inside of the hearing hood, wherein the unit comprises a covering plate for closing the recess.

2. The hearing protector of claim 1, wherein the microphone and an operating device for activating the amplifier are disposed on the covering plate.

3. The hearing protector of claim 1, wherein a portion of the unit around the loudspeaker sealing abuts the bottom wall.

4. The hearing protector of claim 3, wherein the depression is disposed in a recess of the bottom wall, and the sealing abutment of the unit takes place along an edge of the recess.

5. The hearing protector of claim 3, wherein the bottom wall has an opening through which the loudspeaker extends, wherein a sealing ring is disposed around the loudspeaker.

* * * * *

UNITED STATES PATENT AND TRADEMARK OFFICE
CERTIFICATE OF CORRECTION

Page 1 of 1

PATENT NO.         : 8,243,943 B2
APPLICATION NO.    : 10/580923
DATED              : August 14, 2012
INVENTOR(S)        : Henrik Nordin It is certified that error appears in the above-identified patent and that said Letters Patent is hereby corrected as shown below:

Column 3
Line 53, delete "the" and insert -- The -- therefor.

Column 6
Lines 22-29, delete "In one embodiment ............two people.," and insert the same on Col. 6, Line 23, as a New paragraph.

Signed and Sealed this
Eighteenth Day of December, 2012

David J. Kappos
*Director of the United States Patent and Trademark Office*